United States Patent
Raithel et al.

[11] Patent Number: 6,093,551
[45] Date of Patent: Jul. 25, 2000

[54] PROCESS AND DEVICE FOR IN VITRO DIAGNOSIS OF ALLERGIC DISORDERS

[75] Inventors: Martin Raithel, Naabstr. 14, D-92533 Wernberg/Köblitz; Hans-Jürgen Reimann, Ebenhausen, both of Germany

[73] Assignee: Martin Raithel, Wernberg/Koblitz, Germany

[21] Appl. No.: 09/077,872

[22] PCT Filed: Dec. 9, 1996

[86] PCT No.: PCT/EP96/05501

§ 371 Date: Sep. 3, 1998

§ 102(e) Date: Sep. 3, 1998

[87] PCT Pub. No.: WO97/22002

PCT Pub. Date: Jun. 19, 1997

[30] Foreign Application Priority Data

Dec. 8, 1995 [DE] Germany ............... 195 45 920
Dec. 11, 1995 [DE] Germany ............... 295 19 602 U

[51] Int. Cl.$^7$ ............ C12M 1/00; C12M 1/04; C12M 1/38; G01N 33/50; G01N 33/68

[52] U.S. Cl. ............ 435/7.21; 435/23; 435/25; 435/28; 435/29; 435/286.1; 435/296.1; 435/303.1; 435/307.1; 435/374; 435/407; 435/809; 436/71; 436/86; 436/98; 436/513

[58] Field of Search .................. 119/311, 312, 119/318, 319; 435/286.1, 303.1, 307.1, 374, 407, 809, 7.21, 23, 25, 28, 29, 296.1; 436/573, 71, 86, 98

[56] References Cited

U.S. PATENT DOCUMENTS

| | | | |
|---|---|---|---|
| 3,376,405 | 4/1968 | Gower, III | 119/319 |
| 3,712,268 | 1/1973 | Reed | 119/319 |
| 4,188,265 | 2/1980 | Larro | 435/303.2 |
| 4,204,037 | 5/1980 | Forsch et al. | 435/303.1 |
| 4,336,329 | 6/1982 | Hesse et al. | 435/3 |
| 4,780,429 | 10/1988 | Masaaki et al. | 514/382 |
| 4,840,771 | 6/1989 | Williamson et al. | 435/303.1 |
| 5,061,448 | 10/1991 | Mahe et al. | 435/303.1 |
| 5,225,436 | 7/1993 | Neng-Yang et al. | 514/440 |
| 5,449,669 | 9/1995 | Metcalfe et al. | 514/13 |

FOREIGN PATENT DOCUMENTS

WO 90 02741 3/1990 WIPO.

OTHER PUBLICATIONS

Patent Abstracts of Japan, vol. 017, No. 030 (C–1018), Jan. 20, 1993.
Patent Abstracts of Japan, vol. 018, No. 086 (C–1165), Feb. 14, 1994.
Hörauf et al., Agents and Actions, 27:89–92 (1989).
Raithel et al., Agents and Actions, 28: 164–167 (1989).
Raithel et al., Fortschritte der Medizin, 109: 581,585 (1991) (Eng. abstract); abstract only considered.
Raithel et al., IntArchAllergyImmunol, 108: 127–133 (1995).
Raithel et al., Endoscopy, 27: 415–423 (1995).

*Primary Examiner*—David Saunders
*Attorney, Agent, or Firm*—Bacon & Thomas

[57] ABSTRACT

The invention relates to a process for the in vitro diagnosis of allergic, in particular also pseudo-allergic, immunological and environment-related disorders using live biopsy tissue samples. Also disclosed is a mobile incubation device for keeping the tissue samples alive and functioning. The samples can be, for example, skin or mucous membrane particles. The biopsy sample (14) once removed from the patient is placed in a temperature-controlled oxygen-containing incubating medium (16) and an allergen is introduced, triggering an immediate reaction (a so-called type 1 allergy). The secretion of immunoglobulin E (IgE) or a mediator is then determined qualitatively and/or quantitatively. Suitable mediators are histamine, tryptase, ECP, MPO, DAO, TPS, interleukins, prostaglandins or cytokines. The proposed mobile incubation device is provided with a temperature-controllable incubator for sample holders inside a housing. The sample containers can be filled with a nutrient solution. An oxygen-containing fluid is bubbled through feed ducts into the nutrient solution.

13 Claims, 2 Drawing Sheets

PROCESS AND DEVICE FOR IN VITRO DIAGNOSIS OF ALLERGIC DISORDERS

This application is filed under 35 USC 371, based upon International Application Number PCT/EP96/05501, filed Dec. 9, 1996.

The present invention relates to a process for the in vitro diagnosis of allergic, in particular also pseudoallergic, immunological and environment-related disorders using vital biopsy tissue samples, and to a mobile incubation device for maintaining the vitality and functioning of the tissue samples.

A predominant task of the human immune system is to distinguish between endogenous and exogenous substances and, where appropriate, initiate destruction of the exogenous substances.

The progress in the development of immunological methods in the past has repeatedly revealed novel diagnostic and therapeutic possibilities. Thus, for example, highly specific monoclonal antibodies are used as detectors for pathogenic viruses, bacteria and parasites or for detecting pathological cellular alterations. It has additionally been found recently that numerous chronic disorders are attributable to a pathological reaction of the immune system. In so-called autoimmune diseases such as myasthenia, rheumatoid arthritis or else juvenile diabetes, the immune response is directed against endogenous cells and substances. Also to be categorized as pathological are the cases where the body initiates an excessive immune response as a result of contact with an exogenous substance. These hypersensitivities, referred to as allergies, to substances which are innocuous per se, may induce cutaneous and mucosal swelling over the whole body or, in serious cases, life-threatening reactions in conjunction with an anaphylactic shock.

Elucidation of the individual immunological functional processes, especially the diagnosis of the specific reaction of the individual patient to particular allergens, represents a task which is, especially in recent times, becoming increasingly important in medicine.

A large number of very disparate processes are known for detecting allergic reactions:

Thus, for example, tissue samples are routinely taken after operations and during endoscopic investigations. After the tissue samples have been taken they are deprived of nutrients and rapidly die. With suitable staining methods and immunohistological labeling methods it is possible to draw conclusions, from morphological changes and from the detection of particular antigens, about certain allergic reactions. These histopathological methods do not, however, permit any conclusions about the substances which induce an immediate allergic reaction (called a type 1 reaction). Likewise, no statements about the current functioning of the immune cells are possible.

Essentially three different test methods are employed for diagnosing these type 1 allergies:

The most widely used are the so-called skin test methods. These entail extracts of suspected allergens being introduced into the skin by either scratching or pricking, or they are placed on the skin. The locally stimulated allergic reaction is then manifested as reddening and swelling of the affected area of skin.

In immediate-type allergic reactions, immunoglobulin E (IgE) is involved as antibody. This is made use of in the blood test methods in which the amount of IgE in the blood is determined with the aid of radioimmunological or immunoenzymatic methods. These methods not only allow the total amount of IgE in the blood to be determined but also permit allergen-specific immunoglobulins to be determined.

The third method, finally, involves so-called specific provocation procedures in which the allergens are brought into contact directly with the patient's mucosa (for example the nasal or intestinal mucosa) and the reaction is observed.

However, a crucial disadvantage of all three methods is the fact that the patient must be exposed to the allergen. This may, on the one hand, lead to an unwanted renewed sensitization and, on the other hand, in fact induce serious reactions, such as anaphylactic shock, in individual cases.

There is thus an urgent need for a test for type 1 allergies (immediate type) which, on the one hand, permits reliable diagnosis of the reaction to a specific allergen and which, on the other hand, does not lead to the patient being brought into contact with the allergens in the investigation.

U.S. Pat. No. 5,098,831 describes a test method in which whole blood samples from a patient are stimulated in vitro with allergens. The patient is not in this case brought into contact with the allergen. Allergic reactions are established by the detection of histamine released by the leukocytes present in the blood.

However, the disadvantage of the known method is that the histamine determination is on its own a very unreliable indicator of allergic reactions. On the one hand, numerous allergic, pseudoallergic and environmental pollution-related disorders cannot be detected or mutually distinguished by investigating the histamine secretion. On the other hand, determination of other indicators of allergic reactions in whole blood samples is not possible.

To avoid such disadvantages, a test method which makes it possible to stimulate allergic, pseudoallergic or immunological reactions in vital tissue samples in vitro is proposed.

Tissue samples are routinely taken from the patient after operations and during endoscopic investigations. After the tissue samples have been taken they are deprived of nutrients and normally die rapidly. The pathologist is able to draw conclusions about existing or else previous disorders of the patient on the basis of macroscopic and microscopic alterations in the tissue sample or of thin sections of the tissue sample.

However, with usual histopathological methods the information obtainable about the functioning of the tissue samples, that is to say in particular about the functioning of individual cells or the cooperation of different cells in physiological processes, is only very inadequate, if there is any. Particular mention should be made in this connection of the complex processes in the abovementioned immunological or allergic reactions. Thus, although there are immunohistological labeling methods in which conclusions can be drawn about certain allergic reactions, by detecting particular antibodies in tissue sections, these methods fail with so-called type 1 reactions.

Virtually no investigations on vital tissue samples have to date been carried out in medical diagnosis. The reason for this is, inter alia, that, similar to the situation in conventional histopathology, investigation of vital tissue samples requires elaborate instrumentation and correspondingly trained specialist staff, which is not normally available at the place where the tissue sample is taken from the patient. In pathology this is generally not a problem because parts of organs or tissue samples can be preserved, for example, in formalin and the pathologist can carry out his investigations after hours or even days with negligible loss of information. It is thus possible for the samples to be sent from hospitals and primary care physicians to regional specialist centres in which the actual investigations take place.

An analogous procedure would have to be considered for investigating vital tissue samples too. However, this has until now proven impossible because to date there are no suitable devices in existence to allow tissue samples to be transported in an uncomplicated and reliable manner with their vitality being maintained in the transport container for at least some days.

It is therefore an object of the present invention on the one hand to indicate a process which makes in vitro diagnosis of allergic and immunological disorders possible using vital tissue samples. It is moreover intended that the process makes it possible for allergic, pseudoallergic and environmental pollution-related disorders to be identified and mutually distinguished. It is further intended that the novel process be suitable for investigating a large number of other immunological functional processes. These include, in particular, the study of inflammatory processes and of the mechanisms of regulation of the immune response. On the other hand, it is the object of the present invention to provide a mobile incubation device which makes it possible to maintain the vitality and functioning of tissue samples for several hours and up to some days, and thus make it possible to transport the tissue samples from hospitals and primary care physicians to individual centres specializing in the corresponding investigations. It is moreover intended that the novel device be amenable to low-cost production and operation because corresponding investigation methods will become widely used only if the costs associated therewith are kept as low as possible.

The present invention accordingly relates to a process for the in vitro diagnosis of allergic disorders using vital tissue samples, which comprises placing the biopsy tissue immediately after it has been taken from the patient in a temperature-controlled, oxygen-containing incubation medium, adding at least one allergen to the incubation medium for the purpose of stimulating the tissue sample, and determining qualitatively and/or quantitatively the immunoglobulin E (IgE) or a mediator released into the incubation medium after the allergen has acted for a certain time. The detected concentrations of IgE or of a mediator are compared with a negative control, that is to say spontaneous release without allergen stimulation.

The biopsy tissue samples are preferably samples of skin or mucosa, in particular particles of mucosa from the patient's gastrointestinal tract. However, any suitable samples of skin or mucosa can be used. These can be obtained, in particular, by means of biopsy of, for example, the skin, the pulmonary, the intestinal or the gastric mucosa.

It has been found, surprisingly, that even such complex functional processes as allergic or immunological reactions can be stimulated in vitro. This results in the advantage, compared with known in vitro stimulation methods, that a wide variety of cell populations are involved in the allergic reaction and therefore widely different mediators can be detected.

The novel process has the advantage by comparison with conventionally performed biopsy that the tissue sample is, after removal from the patient's body, kept alive, for example by perfusing it with an incubation medium in an incubator, for example the mobile incubation device described hereinafter. Besides the tests normally carried out for morphological and pathophysiological alterations, it is also possible according to the invention to carry out functional physiological and immunological tests, and it is possible to detect lesions and diseases which are not directly manifested by morphological tissue alterations. The diagnostic possibilities of biopsy are thus extended in an advantageous manner. It is clear that, by comparison with conventional allergy tests, with the process proposed according to the invention allergy tests are possible without endangering the patient.

The vital biopsy material can be used in particular for in vitro diagnosis of allergic reactions. This entails making use either of the fact that allergies of the immediate type are associated with an increased production of immunoglobulin E, or of the fact that so-called mediators (messengers) are released in the mucosa during the "allergic attack" and initiate the actual symptoms of the allergic attack.

It is advantageous additionally to determine the total content of mediator in the sample tissue. To this end, the tissue sample is homogenized mechanically together with a defined amount of water in a homogenization tube, fixed aliquots of the homogenate are removed from the homogenization tube, these aliquots are centrifuged, and the particular mediator is quantitatively determined in the resulting supernatants. The homogenization tube is rinsed where appropriate in order to be able also to measure the mediator residues adhering to the walls of the tube. For this purpose, the tube is charged again with the same amount of water, mechanical homogenization is again carried out, and the same aliquots, in terms of amount, of solution are removed from the homogenization tube. The aliquots are centrifuged and, finally, the particular mediator is quantitatively determined in the supernatants. This step of rinsing the homogenization tube and subsequent determination of the amount of the mediator is preferably carried out at least twice, performing the second rinsing step with a protein solution, in particular the incubation medium. The total mediator content in the sample tissue is then obtained by adding the values.

It is possible, by homogenizing the stimulated and unstimulated biopsy material, also to quantify the content of environmental pollutants, besides measuring the cell mediators. This provides an additional idea of the vitality of the immune cells, which permits conclusions about the immune status and allows optimized therapy.

The mediators may be various mediators which are released during allergic reactions and for which detection methods known per se exist. Mediators preferably investigated are histamine, tryptase, ECP (eosinophil cationic protein), MPO (myeloperoxidase), DAO (diamine oxidase), TPS (tissue polypeptide specific antigen), interleukins, prostaglandins or cytokines. The mediator can be detected, for example, by a radioimmunoassay or an ELISA test. Corresponding test methods are commercially available.

To maintain full functional vitality of the tissue sample it is proposed according to the invention to use a modified form of the Hanks and PIPES/RPMI incubation medium.

The Hanks (PIPES/RPMI) solution is commercially available and has, in the case preferred here, a pH of 6.0 and should contain no glycerol, no phenol red, no $MgSO_4 \times 7H_2O$ and no $CaCl_2 \times 2H_2O$.

However, for a preferred incubation medium, the Hanks solution additionally contains 10 to 40 mM Hepes buffer, 0.5 to 2% fetal calf serum and 0.1–0.5% human albumin. Particularly preferred in this connection are 25 mM Hepes buffer, 1.0% fetal calf serum and 0.3% human albumin. In the latter case, this corresponds, for example, to 12.5 ml of Hepes buffer, 5 ml of fetal calf serum and 1.5 g of human albumin in 500 ml of Hanks solution.

The novel incubation medium is distinguished by a high oxygen-binding capacity and a very good pH constancy during aeration with oxygen and has a high nutrient value for the biopsy material. The incubation medium has no toxic effect whatsoever on the tissue.

In order to obtain maximally informative results, the incubation medium is kept at approximately body temperature, that is to say the temperature is in the region of 37° C. The incubation medium is preferably aerated with oxygen in such a way that an oxygen partial pressure ($pO_2$) in the range from 85 to 120 mmHg is set up. The oxygen can be bubbled into the incubation medium from an oxygen cylinder but, in a simpler procedure for the novel process, ambient air is passed through the incubation medium with the aid of a pump, where appropriate through a sterilizing filter. The pH of the incubation medium is advantageously chosen in the region of 7.4. Numerous advantages are associated with the novel process. The most important advantage to be mentioned is that the entire immunological or allergological diagnosis takes place in vitro, that is to say the patient is no longer exposed to potentially harmful substances for the diagnosis. The only unpleasantness for the patient is the need to take a mucosal tissue sample. However, biopsies of this type are nowadays carried out routinely and are completely without danger for the patient. In contrast to cutaneous and blood tests, the stimulation with the allergen takes place in the tissue in which the allergic attack is also induced in the body. Carrying out the diagnosis in vitro makes it possible to comply with standardized conditions which remain the same from investigation to investigation, and thus avoids sources of error which necessarily occur in investigations on the human body. It is also possible at the same time to carry out investigations into the effect of particular medicines, which can be added, for example, to the incubation medium.

The novel process can be supplemented by detection of genetic predispositions to allergic disorders by molecular biological determination of HLA loci, which is of great importance for the prophylaxis of these disorders.

It is, of course, also possible to carry out corresponding investigations on samples of animal tissue. Investigation of cell mediators in the animal body, and detection of environmental pollutants in animal tissue, make it possible to draw conclusions about the possible effects on the human body through the commutability of these substances. Investigations of these types can contribute, for example, to more pollutant-free nutrition of people, especially children.

The present invention additionally relates to a mobile incubation device for maintaining the vitality and functioning of tissue samples, having a compact housing and a lid belonging thereto, having a heatable incubator, arranged in the housing, for sample containers which can be charged with a nutrient solution, having oxygen-supply means which bubble a fluid containing oxygen gas through lines into the nutrient solution in the sample containers, and having energy-supply means which ensure control of the incubator temperature.

The individual sample containers in this case receive tissue samples with a fresh weight of a few milligrams up to a few hundred milligrams in about 2 to 10 ml of nutrient solution. The temperature of the incubator and thus of the nutrient solution is usually kept constant at about 37° C. The oxygen partial pressure in the nutrient solution should be about 85 to 120 mmHg. Because of the small volume of nutrient solution in each sample container, the oxygen consumption is extremely low, so that it is also possible for the oxygen-supply means to be designed to be very compact. The novel mobile incubation device is therefore small and convenient and can, for example, be transported by courier services safely and reliably from physicians and hospitals to central investigation laboratories.

It is moreover possible for a water bath to be used as heat reservoir for the incubator, into which the sample containers are immersed.

However, the incubator advantageously has an element made of a solid material, for example a metal block, in which recesses are excavated to receive the sample containers. This ensures safe transport of the incubation device, and leaks as may occur, for example, with water baths are avoided. However, it is also possible to use blocks of heat-conducting plastic.

Heating elements, for example a resistance heating, can be provided in the incubator for heating thereof. The heat output of the heating elements is advantageously controlled by a thermostat so that the required temperature is kept as constant as possible during the storage of the biopsy material. The novel incubation device can also have control lights which indicate whether a particular temperature range has been complied with during storage of the samples.

The oxygen-supply means may comprise one or more cartridges of a fluid containing oxygen gas. This can be, for example, oxygen or simply compressed air. The cartridges can be rechargeable and are, in this case, refilled before the incubation device is delivered to the physicians anew.

However, it is also possible to provide, in place of the oxygen cartridges, a miniature compressor or a small blower with whose aid ambient air is continuously bubbled into the nutrient solutions.

The oxygen-supply means advantageously have some lines which terminate in a fine-needle nozzle or a sintered disk in the nutrient solution in the sample containers. An essentially efficient oxygen supply to the nutrient solution in this case is the bubbling of gas bubbles which are as small as possible into the solution.

In a particularly simple design of the novel incubation device, the fine-needle nozzle is the needle of a disposable syringe which forms part of the oxygen line system and is inserted into the sample container. The sample container and the syringe system coming into contact with the nutrient solution can be replaced after each use without considerable costs arising thereby.

Suitable and preferred as energy supply for the complete arrangement are batteries or chargeable accumulators.

For monitoring of the principal operating parameters, the novel incubation device has at least one pH-meter and at least one oximeter for controlling respectively the pH and the oxygen content of the nutrient solution in at least one of the sample containers. It can usually be assumed that comparable conditions prevail in the other sample containers. However, it is, of course, also possible to provide corresponding measuring units in all the sample containers. The temperature of the nutrient solutions can be determined directly in the solution or indirectly from the temperature of the incubator.

In order to minimize the energy consumption of the novel device, the housing and the lid consist of a thermally insulating material or are at least lined with an insulating layer.

A typical sequence of the novel process and an example of the novel mobile incubation device are explained in more detail below with reference to the appended drawings.

Figure 1:
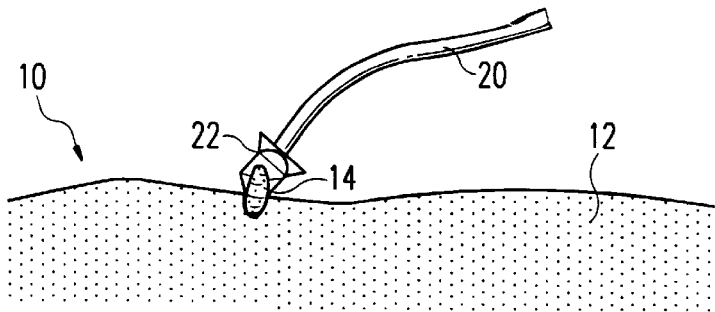
FIG. 1 shows diagrammatically the taking of a tissue sample from a patient's mucosa.

FIG. 1 depicts diagrammatically a patient's intestinal section 10. The inner wall of the intestinal section 10 is covered with a mucosal layer 12. An endoscope 20 is inserted into the intestine and, with visual monitoring, a biopsy tissue sample 14 of the intestinal mucosa 12 is taken by a gripping arm 22 of the endoscope. It is in general unnecessary to anesthetize the patient for this.

A biopsy sample typically has a size of 2–5 mm and a fresh weight between 2 and 150 mg.

Figure 2:
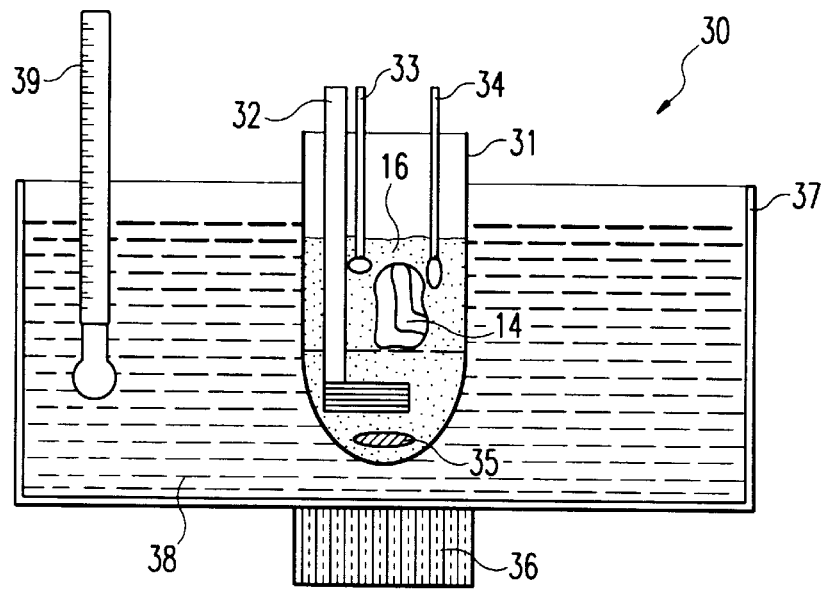
FIG. 2 shows the incubated tissue sample in a temperature-controlled bath.

As depicted in FIG. 2, immediately after taking the biopsy sample 14 it is placed in a prepared incubator 30, called a mucosa oxygenator, where it is supplied with an oxygen-containing incubation medium 16. A Hanks- and PIPES/RPMI-modified incubation medium is used as nutrient solution. About 4 ml of incubation medium 16 are present in an incubation tube 31. The oxygen supply takes place through an oxygen line 32 which terminates in the incubation medium with a sintered disk or fine-needle nozzle attached at the end. The oxygen content of the incubation medium is determined by an oxygen electrode 33 and is preferably adjusted in the range from 85 to 120 mmHg by controlling screws. The pH of the solution is chosen in the region of 7.4 and is monitored by a pH electrode 34 immersed in the incubation medium 16. The incubation tube 31 is immersed in the water 38 of a temperature-controlled bath. The temperature of the water bath is adjusted to 37° C. and is monitored by means of a thermometer 39. The thermometer 39 can be part of a thermostat, in which case additional (not depicted) heating and cooling elements can be provided to keep the temperature of the water constant at the chosen 37° C.

The biopsy sample 14 is then stimulated with an allergen. The allergen can be added in solid, liquid or gaseous form to the incubation medium 16. However, it can also be present in the medium 16 even before the biopsy sample 14 is introduced.

The oxygen ascending in the incubation medium will generally ensure thorough mixing and homogeneous dispersion of the allergen. However, it is also possible where appropriate to provide a miniature stirring bar 35 on the bottom of the tube 31, which is driven by a magnetic stirrer located outside the temperature-controlled bath.

It is clear that it is possible with the novel incubation process to elicit an allergic reaction of a vital biopsy sample 14 without this involving possible disadvantageous effects for the patient. If it is already known that a specific substance has an allergenic effect, it is also possible with the novel process to investigate the therapeutic effect of particular medicines. For example, antihistamines or DSCG (the disodium salt of cromoglycic acid) can be added to the incubation medium in order thus to be able to assess the effect or the activity of these medicines on stimulation by the allergen in vitro.

After a certain incubation time (normally after about 240 min), the concentration of the released mediator in the incubation medium 16 is determined. However, a certain proportion of mediator substances also remains in the tissue 14 itself. To determine the total mediator content, the biopsy sample 14 is homogenized mechanically or by ultrasound. An enzymatic treatment of the biopsy sample can also take place during the homogenization.

For this purpose, the biopsy sample is taken out of the incubation medium and first cooled to −72° C. in order to suppress all metabolic processes and the degradation processes which start.

Figure 3:
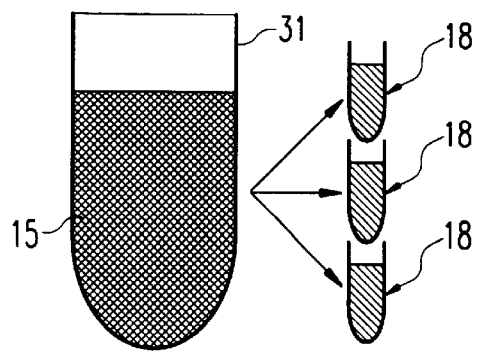
FIG. 3 shows the homogenate of tissue sample and incubation medium.

Mechanical homogenization of a biopsy sample with a fresh weight of 2 to 150 mg together with 1500 µl of double-distilled water at 1500 revolutions/min for 5 minutes provides, for example, 1400 µl of homogenate. Experience has shown that about 100 µl are lost as splashes on the walls and lid of the homogenization vessel. However, this loss can be for the most part recovered by the rinsing of the homogenization vessel described below. The homogenate 15 present in the tube 31 is depicted in FIG. 3 and can be, for example, divided into aliquots 18 for further analysis. In this connection, it has emerged that, starting from the 1400 µl of homogenate, the following amounts are advantageous: 100 µl of homogenate with addition of a further 100 µl of 8% strength perchloric acid for the histamine determination, 400 µl of homogenate for the determination of tryptase, ECP and MPO and, finally, 900 µl for the determination of DAO, TPS and the cytokines. The aliquots are subsequently centrifuged at 7500 revolutions/min and 4° C. for 10 min. The concentration of the mediators in the supernatant is measured.

The homogenization vessels normally used are containers made of polytetrafluoroethylene (Teflon®), on whose walls it is possible for mediator residues or whole and clumps of cells from the homogenate to adhere. It is possible by rinsing twice also to analyze these residues. Firstly, a further 1500 µl of double-distilled water is introduced into the homogenization vessel from which the homogenate has previously been removed. The mechanical homogenizer is in this case operated at 1500 revolutions per minute for 3 minutes. The 1400 µl of rinsing solution which can be removed from the vessel are divided into the aliquots already described above for determination of the individual mediators. The aliquots are centrifuged at 7500 revolutions/min and 4° C. for 10 min. The concentration of the mediators in the supernatant is measured again. The same vessel rinsing process is repeated once again, using in this case 1500 µl of a suitable protein solution, for example the incubation medium itself, as rinsing solution.

Whereas the double-distilled water causes the cells to burst owing to the osmotic pressure, the incubation medium is particularly suitable for detaching cell fragments and mediator residues from the walls of the homogenization vessels usually consisting of Teflon®.

If the specific allergen has induced an allergic reaction, an increased concentration of IgE or of mediators such as histamine, interleukins, prostaglandins or cytokines is expected in the incubation medium or in the homogenate.

Mainly employed for IgE determination are the specific antigens themselves or anti-IgE antibodies. The immune complex produced in the reaction of IgE with the antigen or the anti-IgE antibody then leads as in vivo to the allergic reaction or reaction of the immune cell.

Figure 4:
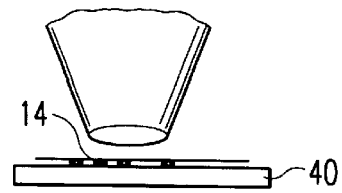
FIG. 4 shows a histological investigation of the unhomogenized biopsy material; and finally

It is also possible, alternatively, as depicted in FIG. 4, to carry out conventional pathological or immunohistological investigations on the specimen.

Routinely, 5 to 15 samples are taken at an endoscopy and are tested.

It is also possible to carry out the entire test in a controlled experiment, but no allergen stimulation takes place in this case. The concentrations of the mediators obtainable in this way are a measure of the spontaneous release thereof.

Figure 5:
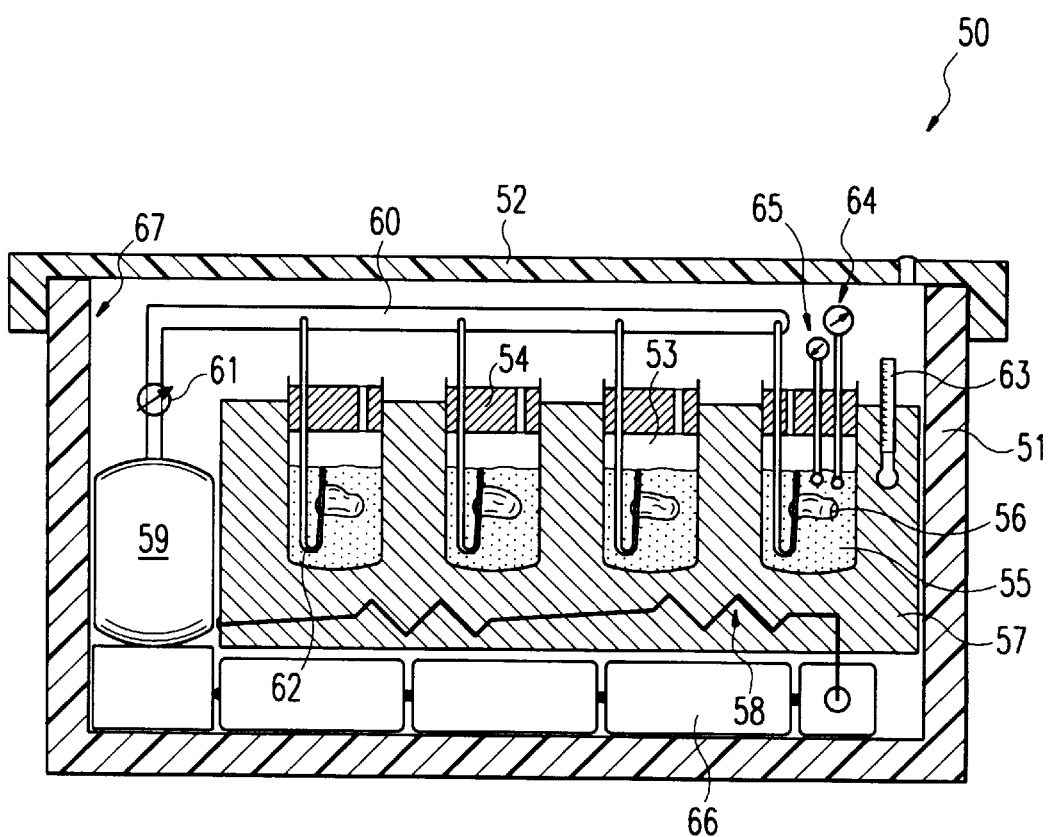
FIG. 5 shows a cross-section through a novel mobile incubation device.

The novel tissue stimulation with allergens can be carried out, for example, in the mobile incubation device described below and depicted in FIG. 5. The incubation device 50 has a box-like housing 51 in which a metal block 57 acting as heat reservoir is located. Cylindrical recesses are excavated in the upper side of the metal block, and sample containers 53 are located therein. The sample containers are closed with liquid-tight stoppers 54. A prepared nutrient solution 55 which is distinguished in particular by a high oxygen-binding capacity is present in the sample containers.

The incubation device 50 additionally contains heating elements 58 for controlling the temperature of the incubator 57, an oxygen supply 59, an energy supply 66, and various monitoring units such as one or more thermometers or a thermostat, one oximeter and pH-meter.

The physician can receive the incubation device, for example, together with sample containers already charged with nutrient solution. The incubator is switched on and indicates by a control lamp when the required temperature, for example 37° C., is reached. The tissue samples 56 taken from the patient are placed in individual sample containers and attached to the oxygen supply 59 via lines 60 and fine-needle nozzles 62. The oxygen supply 59 can be a small oxygen cylinder or else an oxygen cartridge, but it is also possible to provide a small blower which blows air, where appropriate through a sterilizing filter, into the sample containers, the oxygen in this case essentially being the oxygen from the air. It is ensured by an oximeter that the oxygen partial pressure in the nutrient solution is in the range between about 85 and 120 mmHg. The pH of the incubation medium is approximately in the region of 7.4. A restrictor valve 61 provided in the oxygen line 60 ensures maintenance of the required oxygen partial pressure. The energy supply 66, preferably a rechargeable accumulator, serves to supply current to the measuring and display equipment and to the heating elements and, where appropriate, the blower. The housing 51 is advantageously provided with an insulating jacket 67, and the lid 52 used to cover the incubator is also insulated. The energy requirement of the heating elements is thus kept extremely low, and the accumulator can accordingly have a light and space-saving design. The stopper 54 of the sample container may have a semipermeable membrane which allows the oxygen bubbled into the nutrient solution, or the air, through, but retains the moisture carried over from the solution. The stopper 54 may additionally have passages for the oxygen line 60 and, where appropriate, the measurement lines of the oximeter 64 and of the pH-meter 65.

It is possible in practice, for example, to set up a courier service which collects the incubators with the tissue samples in hospitals and from primary care physicians, and delivers thereto again incubation devices ready for use with sample containers containing fresh nutrient solution, charged batteries and charged oxygen or air cartridges. It is self-evident that the novel mobile incubation devices may have a wide variety of sizes, that is to say in particular can contain a varying number of sample containers.

We claim:

1. A portable incubation device for maintaining the vitality and functioning of tissue samples, comprising:
    a compact housing,
    a lid associated with said housing,
    a heatable incubator arranged in said housing, said incubator being adapted to receive sample containers which can be charged with nutrient solution,
    oxygen-supply means comprising a line for bubbling a fluid containing oxygen gas into said nutrient solution in said sample containers,
    energy supply means for supplying energy to said incubator,
    and control means associated with said energy supply means as to ensure temperature control of said incubator.

2. An incubation device as claimed in claim 1, wherein said incubator comprises, as a heat reservoir, a water bath or a metal block with recesses to receive said sample containers.

3. An incubation device as claimed in claim 1, wherein said energy supply means comprise heating elements arranged in said incubator for heating thereof, and wherein said control means comprises a thermostat for controlling the heat output of said heating elements.

4. An incubation device as claimed in claim 1, wherein the oxygen-supply means (59) comprise one or more cartridges of a fluid containing oxygen gas.

5. An incubation device as claimed in claim 1, wherein the oxygen-supply means (59) comprise a miniature compressor or a small blower.

6. An incubation device as claimed in claim 1, wherein the oxygen-supply means (59) have a line (60) which terminates in a fine-needle nozzle (62) or a sintered disk in the nutrient solution (55) in the sample container (53).

7. An incubation device as claimed in claim 6, wherein the fine-needle nozzle (62) is the needle of a disposable syringe which forms part of the oxygen line system (60).

8. An incubation device as claimed in claim 1, wherein the energy-supply means (66) comprise batteries or chargeable accumulators.

9. An incubation device as claimed in claim 1, which comprises at least one pH-meter and at least one oximeter to monitor respectively the pH and the oxygen content of the nutrient solution in at least one of the sample containers (53).

10. A method for in vitro diagnosis of allergic disorders by allergen stimulation of vital biopsy tissues samples which comprises:
    placing the biopsy tissue immediately after it has been taken from the patient in a temperature-controlled, oxygen-containing incubation medium located in a sample container of the incubation device of claim 1, adding at least one allergen to the incubation medium for the purpose of stimulating the biopsy tissue, and
    determining qualitatively and/or quantitatively the immunoglobulin E (IgE) or a mediator released into the incubation medium after the allergen has acted for a certain time.

11. The method of claim 10, wherein the mediators are selected from the group consisting of histamine, tryptase, ECP, MPO, DAO, TPS, interleukins, Prostaglandins and cytokines.

12. The method of claim 10, wherein the incubation medium comprises a mixture of Hanks and PIPES/RPMI incubation medium modified by an addition consisting of
    10–40 mM Hepes buffer,
    0.5–2% fetal calf serum and
    0.1–0.5% human albumin.

13. The method of claim 12, wherein the Hanks solution addition consists of
    25 mM Hepes buffer,
    1.0% fetal calf serum, and
    0.3% human albumin.

* * * * *